United States Patent
Baikoff

(10) Patent No.: US 6,719,792 B2
(45) Date of Patent: Apr. 13, 2004

(54) IMPLANT FOR THE CORRECTION OF PRESBYOPIA IN PHAKIC EYES

(75) Inventor: Georges Baikoff, Marseilles (FR)

(73) Assignee: Novartis AG, Basel (CH)

(*) Notice: Subject to any disclaimer, the term of this patent is extended or adjusted under 35 U.S.C. 154(b) by 0 days.

(21) Appl. No.: 09/971,391

(22) Filed: Oct. 4, 2001

(65) Prior Publication Data

US 2002/0019667 A1 Feb. 14, 2002

Related U.S. Application Data

(63) Continuation of application No. PCT/FR00/00815, filed on Mar. 31, 2000.

(30) Foreign Application Priority Data

Apr. 2, 1999 (FR) .............................................. 99 04136

(51) Int. Cl.⁷ .................................................. A61F 2/16
(52) U.S. Cl. .................... 623/6.28; 623/6.36; 623/6.44; 623/6.54
(58) Field of Search ....................... 623/6.33, 6.23–6.31, 623/6.36–6.38, 6.43, 6.44

(56) References Cited

U.S. PATENT DOCUMENTS

| | | | |
|---|---|---|---|
| 4,441,217 A | * | 4/1984 | Cozean ...................... 623/6.43 |
| 4,955,902 A | | 9/1990 | Kelman |
| 5,766,245 A | | 6/1998 | Fedorov et al. |
| 5,769,890 A | | 6/1998 | McDonald |
| 6,358,280 B1 | * | 3/2002 | Herrick ...................... 623/6.26 |

FOREIGN PATENT DOCUMENTS

| | | | | |
|---|---|---|---|---|
| RU | 2 017 471 C1 | * | 8/1994 | ............. A61F/2/16 |
| RU | 2 080 839 C1 | * | 6/1997 | ............. A61F/2/16 |
| US | 4932971 | * | 6/1990 | ................. 623/6.34 |
| WO | WO 99/34752 | | 7/1999 | |

* cited by examiner

Primary Examiner—David H. Willse
(74) Attorney, Agent, or Firm—Gardner Groff, P.C.

(57) ABSTRACT

Ocular implant of the type comprising an optical portion to which there is connected a haptic portion arranged to position the focal axis of the optical portion off-center with respect to the geometric axis of the eye, towards the nasal side, provided for insertion into a phakic eye to correct presbyopia, its optical portion having, at least in its central region (7), a multifocal treatment constituting an addition of from +1 to +3.5 diopters, and its haptic portion (6) ensuring that the focal axis (9) of the optical portion (5) is arranged from 0 to 0.75 mm off-center when the implant is in position in the eye.

9 Claims, 2 Drawing Sheets

IMPLANT FOR THE CORRECTION OF PRESBYOPIA IN PHAKIC EYES

This is a con of PCT/FP00/00815 filed Mar. 31, 2000 which claims foreign priority 99.04136 filed Apr. 2, 1999.

The invention relates to the correction of presbyopia.

The said defect is a loss of accommodation affecting the entire population, starting from the age of about forty. It is manifested in a reduction in the acuity of near vision and is generally corrected by wearing positive convergent glasses that allow images that formerly formed behind the retina to be focussed on the retina.

Emmetropic individuals often feel, however, that having to wear spectacles of that type on a permanent basis is a nuisance and unsightly.

In order to avoid those disadvantages, it is known for the presbyopia to be treated surgically by carrying out remodelling of the cornea with the aid of a laser beam apparatus known by the commercial designation Excimer. The remodelling can be performed on the surface or lower down within the corneal stroma, a technique known by the name of Lasik. However, with living tissue, the scarring of which is unpredictable, it is difficult to produce very accurate curvatures in very small areas. The results of these techniques are the subject of much debate.

More recently, another means of surgically treating presbyopia has been proposed, by implanting on the sclera, in line with the ciliary body, segments that have the function of retensioning the zonule.

It is also known for aphakic eyes to be fitted with posterior chamber implants which are placed either within the capsular sac or in the sulcus and the optical portion of which is termed multifocal because it is treated to allow near vision and vision that is intermediate between near vision (30 cm) and distance vision (from 3 m).

U.S. Pat. No. 4,955,902 furthermore discloses an ocular implant provided for correcting substantial myopia in an eye having an off-center pupil. The implant is positioned in the anterior chamber of the eye; it comprises an optical portion having a concave face and a thick external periphery matched to the correction of the myopia and a dissymmetrical haptic portion allowing the said optical portion to be so positioned that its focal axis is arranged off-centre with respect to the geometric axis of the eye, towards the nasal side.

However, to the knowledge of the Applicant, no-one has until now envisaged or suggested treating presbyopia in emmetropic phakic eyes y means of implants arranged in the anterior chamber or posterior chamber, in the manner of implants currently used for correcting ametropias such as myopia, astigmatism or hypermetropia.

The aim of the present invention is to propose such an implant for an emmetropic phakic eye.

According to the invention, this implant, which comprises an optical portion and a haptic portion arranged to position the focal axis of the said optical portion off-centre with respect to the geometric axis of the eye, towards the nasal side, is characterised in that it is provided for insertion into a phakic eye to correct presbyopia, its optical portion having, at least in its central region, a multifocal treatment constituting an addition of from +1 to +3.5 dioptres, and its haptic portion ensuring that the optical axis of the central portion is arranged from 0 to 0.75 mm off-centre when the implant is in position in the eye.

For a better understanding of the invention, two embodiments of the invention shall be described hereinbelow, with reference to the attached drawings, in which:

FIG. 1 is a diagrammatic partial section of the front portion of the right eye, line 10 denoting the nasal side.

Figure 1:
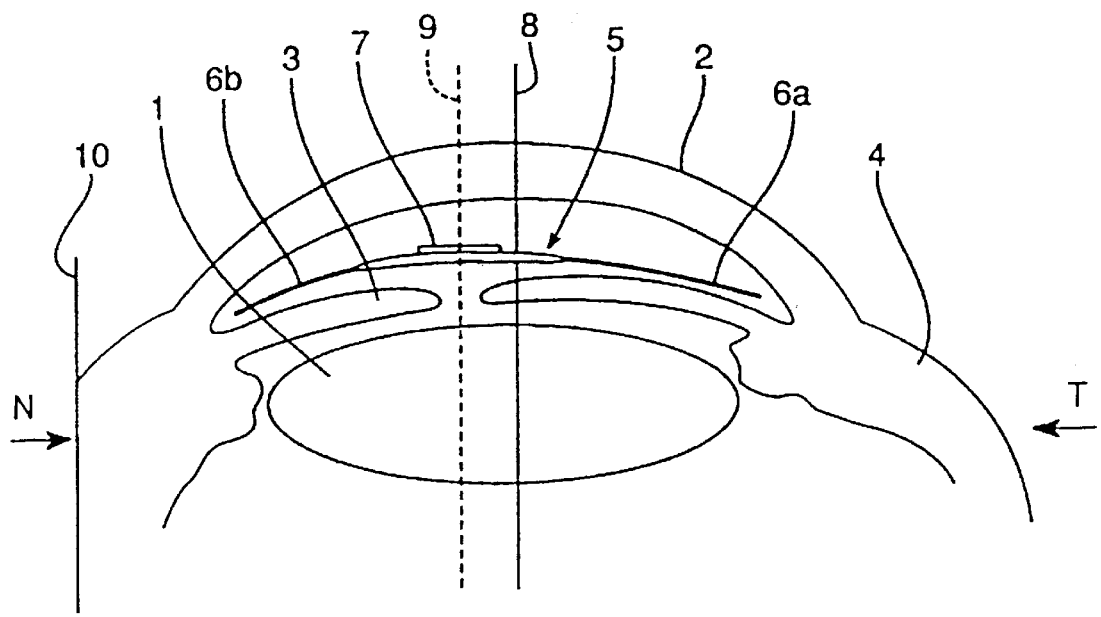
FIG. 1 is a sectional view, in diagrammatic form, of an implant according to the invention inserted in the anterior chamber of the eye.

In the diagram, 1 is the lens of the eye, 2 the cornea, 3 the iris and 4 the sclera. Line 8 represents the geometric axis of the eye; the broken line 9 represents the optical axis, which is determined by the centre of the pupillary orifice and which is arranged off-centre with respect to the axis 8, towards the nasal side.

The arrows N and T denote the nasal and temporal sides of the eye.

Located in the anterior chamber, and lodged in the angle of the iris and the cornea by means of its handles 6a and 6b, is an implant according to the invention.

Its optical portion is composed of a disc 5 of optical material (PMMA, silicone, acrylic material, etc.) of zero focal power, which in this example has, in section, a slight concavity to the rear, matching that of the iris 3.

In its central region, the disc 5 has a multifocal corrective region 7, the power of which is calculated to add a correction of from +1 to +3.5 dioptres depending upon the addition necessary to offset the presbyopia.

The multifocal corrective lens can be constructed in a manner known per se by modifying the central radius of curvature in a very small region of from 2 to 3 mm in diameter which can be connected to the disc 5 by any means. The radius of curvature of this lens 7 can be uniform or can have progressions to provide a central area that is termed progressive. This lens 7 can also be constructed by means of a succession of concentric modifications of the radius of curvature, alternating distance afocal regions and near focal regions, it being possible for the distance vision to be placed at the centre of or at the periphery of the optical axis of the lens. The lens 7 can also be constructed in the manner of a Fresnel lens, having afocal faces and faces overcorrected by from +1 to +3.5 dioptres.

Figure 2:
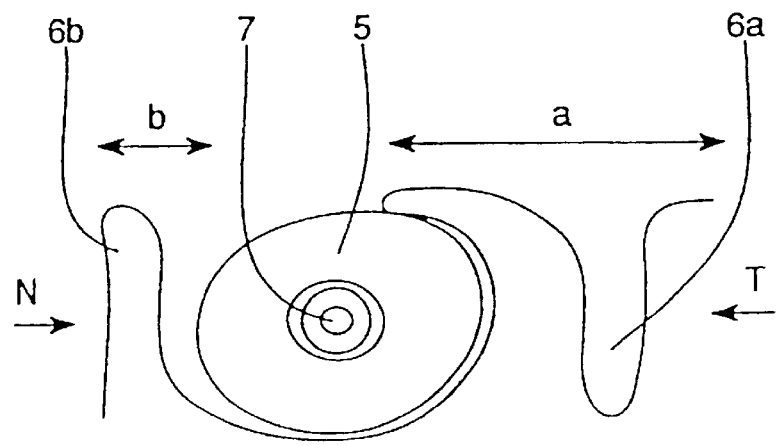
FIG. 2 is a plan view of the implant of FIG. 1.

Connected to the periphery of the disc 5, which constitutes the optical portion of the implant, are the handles 6a and 6b, which constitute Its haptic portion FIG. 2 shows that the length b of handle 6b, which corresponds to the nasal side of the eye, is less than the length a of the handle 6a opposite.

The difference in distance between a and b is adjusted to correspond to the value of the off-centring between the geometric axis and the optical axis of the eye that is to be corrected. As a result, when the implant is in position in the eye, the multifocal region will be correctly centred over the optical axis 9.

On average, the value of the off-centering of the optical axis with respect to the geometric axis of the eye is 0.5 mm, although that value is liable to vary from 0 to 0.75 mm from one individual to another. It is therefore possible for the centring of the multifocal portion to be modified in dependence upon the morphology of each eye.

Consequently, the invention encompasses implants whose haptics are arranged to have, when in positon in the eye, a difference in length that is between those two values (from 0 to 0.75 mm).

Figure 3:
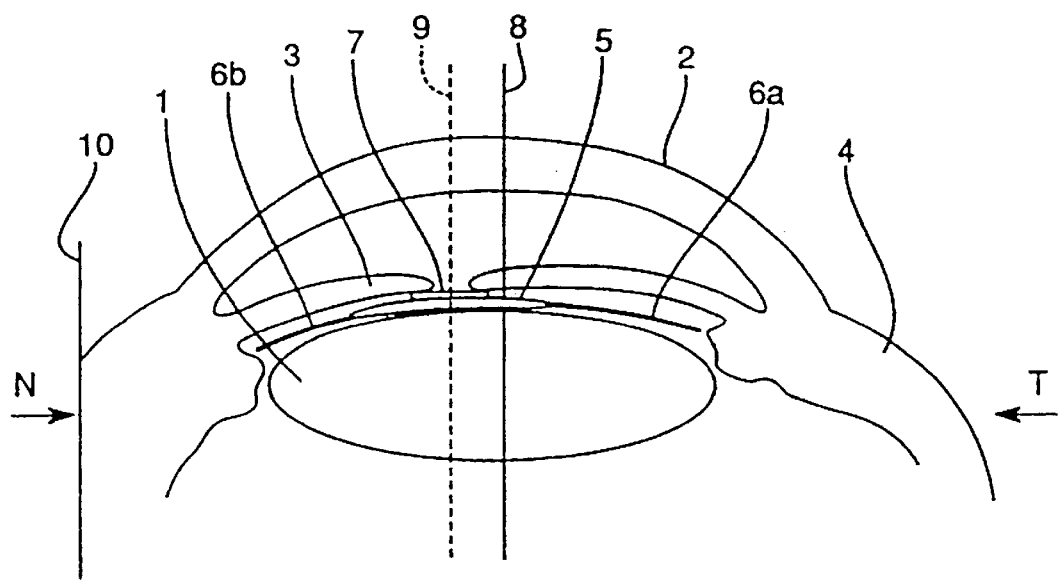
FIG. 3 is a sectional view, in diagrammatic form, of an implant according to the invention inserted in the posterior chamber of the eye.
Figure 4:
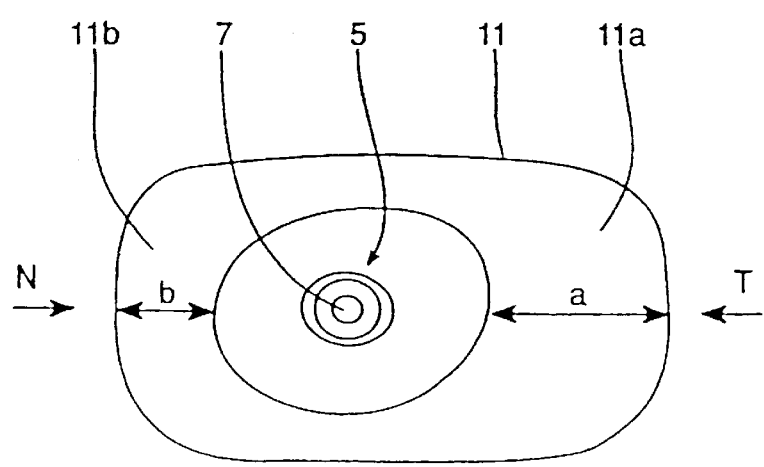
FIG. 4 is a plan view of the implant of FIG. 3.

FIGS. 3 and 4 show an implant according to the invention provided for insertion into the posterior chamber. The reference symbols remain the same as those in FIGS. 1 and 2 for identical parts.

It can be seen that, in contrast to the previous example, the haptic portion of the implant is constructed, not from two diametrically opposite handles, but from a sheet of substantially rectangular shape 11 integral with the optical portion 5, which divides the said sheet 11 into an outer portion 11a and a nasal portion 11b. The distance b separating the edge of the nasal portion from the edge of the optical portion 5 is less than the distance a which separates the outer portion from the corresponding edge of the optical portion 5. As before, the value of that difference in distance is from 0 to 0.75 mm.

The implants according to the invention can have haptic portions in a great variety of shapes (C-shaped handles, J-shaped handles, Z-shaped handles, rings etc.) provided that the off-centring condition is respected.

The invention is also applicable to implants which simultaneously combine a central multifocal region for the treatment of near vision and intermediate vision and a peripheral region suitable for the treatment of myopia, astigmatism and/or hypermetropia.

By way of example, for an implant having an overall diameter, including the haptic portion, of the order of from 12 to 14 mm, the optical portion will have a diameter of the order of from 5 to 6 mm and the central zone of that optical portion will generally have a diameter of from 2 to 4 mm.

However, it is possible, without departing from the scope of the invention, to have an implant for an emmetropic eye, wherein the entire surface of the optical portion is multifocal.

What is claimed is:

1. An ocular implant for correcting presbyopia in a phakic eye having a geometric axis, an anterior portion, and a posterior portion, the implant comprising:
   a haptic portion, comprising:
     a temporal haptic; and
     a nasal haptic; and
   an optical portion having a focal axis, wherein the implant is configured such that upon proper placement of the implant into the eye, the focal axis of said optical portion is positioned from greater than 0 to 0.75 mm off-center toward the nasal haptic in relation to the geometric axis of the eye, said optical portion further comprising a central region having a multifocal treatment comprising an addition or overcorrection in the range from +1 to +3.5 dioptres.

2. An implant according to claim 1, wherein the implant is provided for positioning in the anterior portion of the eye.

3. An implant according to claim 1, wherein the implant is provided for insertion into the posterior portion of the eye.

4. An implant according to claim 1, wherein the optical portion comprises a multifocal central region and an afocal peripheral region.

5. An implant according to claim 1, wherein the optical portion comprises a multifocal central region and a focal peripheral region suitable for the treatment of myopia and/or astigmatism and/or hypermetropia.

6. An implant according to claim 1, wherein the haptic portion is composed of handles.

7. An implant according to claim 1, wherein the haptic portion is composed of a sheet of substantially rectangular shape.

8. An implant according to claim 1, wherein the implant's overall diameter is from 12 to 14 mm, that of its optical portion is from 5 to 6 mm and that of its multifocal central region is from 2 to 4 mm.

9. An ocular implant for the correction of presbyopia in a phakic eye having a geometric axis and a nasal side, the implant comprising:
   a haptic portion; and
   an optical portion having a focal axis, wherein the implant is arranged so that when the implant is positioned in the eye, the focal axis of said optical portion is positioned from greater than 0 to 0.75 mm off-center toward the nasal side in relation to the geometric axis of the eye, said optic portion further comprising a central region having a multifocal treatment comprising an addition or overcorrection in the range from +1 to +3.5 dioptres.

* * * * *